United States Patent [19]

Bornstein et al.

[11] 4,002,748

[45] Jan. 11, 1977

[54] METHOD OF PREPARING STERILE ESSENTIALLY AMORPHOUS CEFAZOLIN FOR RECONSTITUTION FOR PARENTERAL ADMINISTRATION

[75] Inventors: Michael Bornstein; Sandra M. Carone, both of Indianapolis, Ind.

[73] Assignee: Eli Lilly and Company, Indianapolis, Ind.

[22] Filed: Jan. 19, 1976

[21] Appl. No.: 650,210

[52] U.S. Cl. ............................................. 424/246
[51] Int. Cl.² ........................................ A61K 31/54
[58] Field of Search ...................... 424/115, 246; 260/243 C

[56] References Cited

UNITED STATES PATENTS

| | | | |
|---|---|---|---|
| 3,303,193 | 2/1967 | Godfrey | 424/246 X |
| 3,335,136 | 8/1967 | Flynn | 424/246 X |

OTHER PUBLICATIONS

The Merck Index, 8th Edition, p. 222, (1968).

*Primary Examiner*—Albert T. Meyers
*Assistant Examiner*—Daren M. Stephens
*Attorney, Agent, or Firm*—Ralph W. Ernsberger; Everet F. Smith

[57] ABSTRACT

Sterile, essentially amorphous cefazolin sodium for parenteral administration, having an improved solubility on reconstitution, is prepared by a freeze-drying process wherein a sterile solution of from about 10 to about 25 percent (W/V) of cefazolin sodium is exposed to an environment wherein the temperature is held at from about minus 50° C. to minus 55° C. until the temperature of the solution (frozen) is reduced to minus 48° C. to minus 55° C. before subjecting said frozen solution to a high vacuum and a moderate amount of heat to sublime the water therefrom.

2 Claims, No Drawings

METHOD OF PREPARING STERILE ESSENTIALLY AMORPHOUS CEFAZOLIN FOR RECONSTITUTION FOR PARENTERAL ADMINISTRATION

BACKGROUND OF THE INVENTION

1. Field of the Invention

This invention is directed to an improved freeze-drying (lyophilization) process. More specifically, the instant invention concerns a freeze-drying process wherein cefazolin sodium for reconstitution for parenteral administration is prepared which is sterile, essentially amorphous and has good solubility characteristics on reconstitution with water for injection.

2. Prior Art

Freeze-drying is an old and often used process for removing a solvent from a solute. While the process is cumbersome, expensive and slow, it provides a method for removing a solvent without damaging heat labile solutes. Antibiotics and other pharmaceuticals have been processed by freeze-drying procedures for three or more decades and foods, particularly instant coffee, have been prepared by this method for many years. Ordinarily, a solution from which it is desired to recover the solute in a relatively solvent-free state is frozen solid and then subjected to an environment of a high vacuum and the temperature of the environment is raised to provide the units of heat absorbed in the sublimation of the solvent from the frozen solution. The temperature of the environment is kept below that which would result in the meltdown of the frozen solution. In practice, the temperature of the environment is coordinated with the vacuum to produce the highest reasonable sublimation rate, avoiding a melting of the frozen mass.

Water is the solvent generally utilized in a freeze-drying process. Other solvents can be employed but are limited to those which become solid in the range of temperatures which can be practically employed in the process and which will sublime under vacuum.

Although all of the material does not have to be in solution to effectively operate a freeze-drying process, instant coffee being one probable example, this invention is concerned with a process wherein amorphous material is prepared in a freeze-drying procedure from a true solution. In freeze-drying antibiotics and other pharmaceuticals it has been the practice to follow the classic process outlined above; to wit, prepare solution, freeze to solid, subject to high vacuum, add heat, sublime solvent. However, when such a conventional procedure is followed, some compounds come out as amorphous material, others as crystalline material, and still others as a mixture of amorphous and crystalline solids.

The cefazolin sodium involved in this invention can be prepared as crystalline material by utilizing a freeze-drying process such as that described in pending U.S. Patent application Ser. No. 567,224. The crystalline cefazolin sodium prepared by such process has good storage stability and pharmaceutical elegance. However, such cefazolin, while it is adequately soluble, as the sodium salt, in water for injection, is slow going into solution requiring as much as 2½ minutes to dissolve 1.0g. in 2.5 ml of water with vigorous shaking at 25° C.

Crystalline cefazolin sodium can also be recovered from organic solvents, such as ethanol. Such crystals require about the same amount of time to dissolve in water for injection as crystals obtained from a freeze-drying process.

It was found, quite surprisingly, that amorphous cefazolin sodium obtained by recovering such material from organic solvents by evaporating solutions of cefazolin sodium in such solvents to dryness could be dissolved in water for injection in about half the time required to obtain complete solutions of the crystalline material.

An approximate 50 percent reduction in the time required to effect the complete solutioning of cefazolin sodium comprises a significant improvement in that the time that a physician, nurse or paramedic would devote to the reconstitution of a vial of cefazolin sodium for parenteral administration would be substantially lessened, increasing the amount of time available for other activities.

However, utilizing amorphous cefazolin sodium recovered from solution by evaporating the solvent therefrom in sterile ampoule preparations for parenteral administration poses other problems and conditions which are both inefficient, difficult and costly. For example, there is no effective way known to sterilize amorphous cefazolin sodium recovered from a solution by evaporation so the entire process must be carried out in an aseptic environment. In the large and extensive process required to sterilely recover the cefazolin sodium there are many opportunities for the admittance of foreign substances into the material which later on will show up as suspended material in a reconstituted ampoule of the antibiotic. No one has yet developed an apparatus for filling dry material into an ampoule which will measure the material going into each ampoule with as good a consistency and precision as can be routinely achieved with liquid filling equipment.

Accordingly, it is an object of this invention to provide a process of freeze-drying cefazolin sodium that will result in sterile, essentially amorphous, cefazolin sodium for parenteral administration.

Another object of this invention is to provide a process which will include the filling of a measured volume of a sterile aqueous solution of a known concentration of cefazolin sodium into an ampoule wherein such cephalosporin is recovered from such solution as an essentially amorphous material for parenteral administration which is relatively rapidly soluble upon reconstitution with water for injection.

Still another object of this invention is to provide an ampoule containing an essentially amorphous cefazolin sodium which is storage stable and which upon reconstitution for parenteral administration is substantially free of foreign suspended material.

SUMMARY

Now it has been discovered that a storage stable, sterile, essentially amorphous cefazolin sodium for reconstitution for parenteral administration, having a relatively rapid solubility upon reconstitution with water for injection, can be prepared by a freeze-drying procedure comprising the following steps: (a) Cefazolin sodium is dissolved in water in a concentration of between about 10 and about 25 percent. (b) The preparation from (a) is sterile filtered into a previously sterilized container. (c) The preparation from (b) is placed in an environment wherein the temperature is between about minus 50° C. and minus 55° C. (d) The preparation from (b) is maintained in the environment of (c) until all of the solution has frozen and the temperature thereof has been reduced to minus 48° C. or below. (e) The preparation from (d) is stabilized at minus 48° C. or below for 30 minutes. (f) The stabilized preparation from (e) is subjected to a vacuum of 100 microns Hg or less. (g) After the vacuum is stabilized at 100 microns Hg or below, the temperature of the environment in which the preparation from (f) is held is increased to about 10° C. (h) The preparation from (g) is maintained in an environment of about 10° C. and at an absolute pressure of 100 microns Hg or less until such preparation is raised to a temperature of about 5° C. or higher. And, (i) the temperature of the environment in which the cefazolin sodium preparation is maintained at a maximum of 100 microns Hg absolute is raised to 35° C. and maintained there at, subliming the water from the cefazolin sodium preparation resulting in the recovery of an essentially amorphous material having a moisture content of not more than 6.0 percent.

DESCRIPTION OF THE PREFERRED EMBODIMENTS

The useful process of the present invention comprises a procedure utilizing a freeze-drying operation to convert an aqueous preparation of cefazolin sodium, represented by the following structural formula:

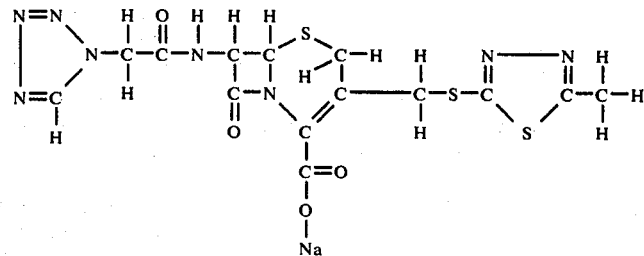

to a sterile, amorphous material for reconstitution with water for injection for parenteral administration. The accepted chemical name for cefazolin, a member of the class of useful antibiotics known as cephalosporins, is 3[[5-methyl-(1,3,4-thiadiazol-2-yl)-thio]-methyl]-7-[2-(1H-tetrazol-1-yl)acetamido]-3-cephem-4-carboxylic acid. It is marketed around the world as the sodium salt. Cefazolin is indicated in the treatment of respiratory tract infections due to *D. pneumoniae*, Klebsiella spp. and others; genitro-urinary tract infections due to *E. coli*, *Proteus mirabilis*, Klebsiella spp., and others and *Staph aureus infections in general*.

The essential element of this invention is the development of the sterile amorphous cefazolin sodium as the solvent is sublimed from a frozen solution of the antibiotic. This is accomplished by controlling the concentration of the cefazolin sodium in the solution from which the amorphous material is to be recovered to from about 10 to about 25 percent, and subjecting such a solution to an environment wherein the temperature is held at between about minus 50° C. and minus 55° C. At such a temperature the solution freezes rapidly and the temperature of the frozen solution is lowered to about minus 48° C. or below in from 1 to 3 hours. It is essential that the temperature of the frozen solution reach about minus 48° C. or below before the sublimation of the solvent is begun. Such a temperature assures that the cefazolin sodium is essentially all in the emorphous state before the removal of the solvent is commenced.

Following the critical steps just described, conventional freeze-drying is employed to sublime the solvent leaving sterile essentially amorphous cefazolin sodium a moisture content of no more than 6 percent. Such cefazolin sodium has a suitable storage stability; two years or more at room temperature, and has an average reconstitution time of from about 50 to about 70 seconds to effect the complete solutioning of 1.0 g. in 2.5 ml of water for injection at 25° C. This compares with an average reconstitution time of about 116 seconds for crystalline cefazolin sodium under similar conditions.

In one aspect of the present invention a sterile, essentially amorphous cefazolin sodium for reconstitution for parenteral administration is prepared by a method comprising the following steps: (a) The cefazolin sodium is dissolved in water in a concentration of from about 10 to about 25 percent (W/V). (b) The aqueous cefazolin sodium preparation from (a) is filtered through a sterilizing filter into a previously sterilized container. (c) The preparation from (b) is placed in an environment wherein the temperature is from about minus 50° C. to about minus 55° C. (d) The preparation from (c) is rapidly cooled to a temperature of about minus 48° C. or below, and allowed to stabilize for about 30 minutes after reaching minus 48° C. (e) The preparation from (d) is subjected to a vacuum of 100 microns Hg or less and allowed to stabilize at an absolute pressure of no more than 100 microns Hg for about 30 minutes. (f) The temperature of the environment to which the preparation from (e) is exposed is raised to about 10° C. and maintained until such preparation reaches about 5° C. (g) The temperature of the environment to which the preparation from (f) is exposed is raised to about 35° C., avoiding the melting of such preparation. And, (h) the ice is sublimed from the preparation from (g) until the resulting amorphous cefazolin sodium has a moisture content of no more than 6 percent.

The cefazolin sodium used in the useful process of this invention should be of a pharmaceutical grade. Such cefazolin sodium is dissolved in water in concentrations of from about 10 to about 25 percent to provide the aqueous solution used in the process detailed herein. Actually, the more dilute solutions provide the greater assurance of obtaining essentially amorphous sterile cefazolin sodium for reconstitution for parenteral administration. However, it is important to balance the concentration of the antibiotic in the solution with the size and configuration of the container into which the solution thereof is to be filled. Moreover, as those skilled in the art of freeze-drying know, the greater the quantity of water which must be sublimed, the greater the cost of the operation.

The sterilization of the aqueous solution of cefazolin sodium can be achieved by filtering such solution through sterile filtering means known to those skilled in the art and collecting the filtrate in a previously sterilized container. Illustratively, sterile filtering can be effected using a heat sterilized plate and frame filter press equipped with an asbestos pad, or a filtering membrane of cellulose acetate or nitrate, or a candle having a porosity below 0.22 um.

A conventional freeze-dryer is comprised of a chamber structurally designed to withstand the application of a high vacuum thereto. In addition, the chamber is outfitted with a plurality of horizontal shelves through which a heat exchange medium is circulated. The container holding the solution to be freeze-dried is placed on a shelf in the chamber and a refrigerant circulating inside of such shelf cools the solution in the container. In the novel process of this invention the refrigerant circulating in the shelf is maintained at a temperature of from about minus 50° C. to about minus 55° C., and the exterior surface of the shelf is equilibrated with the temperature of the refrigerant before, and this is important, the container with the solution to be freeze-dried is placed thereon. This results in an immediate and rapid freezing of the cefazolin sodium solution. Moreover, the frozen solution is exposed to the minus 50° C. to minus 55° C. environment until the temperature of such solution reaches minus 48° C. or below; and even after that the frozen solution is stabilized for another 30 minutes before the subliming operation is commenced. This assures that essentially all of the cefazolin sodium remaining after the water has been sublimed away will be amorphous.

In actual practice it is customary to provide thermocouples at strategic points in the frozen mass to indicate the temperature at this point in such mass. In any event, those skilled in the art will appreciate that consistent temperatures on the refrigerant and times of exposure of the frozen solution to the minus 50° C. to minus 55° C. environment will result in a consistent temperature of the frozen mass.

Once the minus 48° C. or below temperature of the frozen mass has been achieved and such temperature stabilized for about 30 minutes, the physical conditions conducive to the amorphous cefazolin sodium has been established. The rapid freezing of the cefazolin solution and the subsequent lowering of the temperature of the frozen mass to minus 48° C. or below avoids the production of dendritic ice crystals and the consequent nucleation of cefazolin sodium crystals.

After the temperature of the frozen mass of cefazolin sodium solution has stabilized at minus 48° C. or below, a conventional freeze-drying operation is utilized to sublime the ice from the frozen mass leaving a deposit of sterile, essentially amorphous cefazolin sodium.

The cefazolin sodium preparation is subjected to an environment where the pressure can be reduced to a practical maximum of no more than 100 microns Hg absolute. It is preferable to reduce the pressure much more than to 100 microns Hg absolute. The best results are obtained with an absolute pressure of between about 10 microns and about 50 microns. This latter pressure range is ordinarily readily attainable in both laboratory and commercial freeze-drying apparatus, the design, construction and operation of which are all well known to those skilled in the art. After the pressure of the environment described above has been reduced to an operating level, heat is introduced into such an environment. The temperature of the environment is raised to a point where the maximum sublimation rate can be achieved without melting the frozen mass. As a general rule, the temperature and the pressure are inversely related; the more effective the pressure reduction, the higher the temperature which can be employed in the subliming operation. As a common guide it can be said that a maximum environment temperature of 50° C. can be reached with a highly efficient vacuum system where the absolute pressure is maintained at about 50 microns absolute. In any event, the temperature in the useful process of this invention should be raised slowly to avoid overloading the pressure-reducing system which can produce an undesirable melting of the frozen mass. Preferably, the temperature of the environment in the subliming operation should be raised to about 10° C. after the pressure of such environment has stabilized at 100 microns Hg absolute or below. This is accomplished by substituting water circulating at about 10° C. through the shelves for the refrigerant used to lower the temperature of the frozen mass to minus 48° C. or below.

The 10° C. temperature of the environment is maintained until the frozen cefazolin sodium preparation reaches about 5° C., and then the temperature of the environment is raised to about 35° C. This is achieved by replacing the circulating 10° C. water in the shelves with water at about 35° C. The environmental temperature is maintained at about 35° C. until the temperature of the residual cefazolin sodium preparation reaches a temperature of about 30° C. and for an additional 60 to 90 minutes thereafter. Subliming of the ice from the frozen mass as described above results in a moisture content of the amorphous cefazolin sodium of below about 6 percent.

The cefazolin sodium prepared as detailed above is essentially amorphous. For example, physical analyses indicated a crystallinity of between about < 1 and 5 percent, consequently between about 95 and 99+ percent of the cefazolin sodium was amorphous. In any event, a sufficiently high amount of amorphous material was obtained to lower the solubility rate by almost 50 percent when compared with crystalline cefazolin sodium. Moreover, the resulting amorphous cefazolin sodium was stable microbiologically when stored at room temperature for two years. The amorphous cefazolin sodium can be sterile filled into previously sterilized ampoules in appropriate quantities for reconstitution for parenteral administration.

In another aspect of this invention the procedure outlined and discussed in detail hereinbefore is augmented by an additional step which comprises filling a measured volume of the sterile aqueous solution from step (b) into a previously sterilized ampoule, such measured volume containing the quantity of the cefazolin sodium which is desired in such ampoule after the freeze-drying operation. The ampoules containing the sterile aqueous solution of the cefazolin sodium are then processed in the same manner as described above. The resulting freeze-dried cephalosporin ampoule is ready for sterile stoppering and capping. Such an ampoule is ready to be reconstituted with water for injection to provide a suitable dosage form for parenteral administration.

In practice it is preferred to sterile fill a measured volume of the sterile aqueous solution into a previously sterilized ampoule as at least two beneficial results are obtained. First, a more precise and consistent quantity of the cefazolin sodium can be filled into an ampoule in the liquid form than in the solid (crystals or powder) form. And, second, it is much easier to achieve and maintain sterile operating conditions in liquid filling operations than in dry filling operations. Moreover, air pollution is less of a problem when handling liquids than dry materials.

What is claimed is:

1. A method of preparing a sterile, essentially amorphous cefazolin sodium for reconstitution for parenteral administration comprising the steps of:
   a. dissolving said cefazolin sodium in water in a concentration of from about 10 to about 25 percent (W/V);
   b. filtering the solution from a) through a sterilizing filter into a previously sterilized container;
   c. exposing the preparation from b) to an environment wherein the temperature is from about minus 50° C. to about minus 55° C.;
   d. cooling the preparation in the environment of c) to a temperature of minus 48° C. or below and stabilizing for about 30 minutes at such temperature;
   e. reducing the pressure of the environment in which the preparation from (d) is maintained to a maximum of 100 microns Hg absolute, and stabilizing such pressure for about 30 minutes;
   f. raising the temperature of the environment in which the preparation from (e) is maintained to about 10° C. and holding such temperature until the temperature of such preparation reaches about 5° C., avoiding the melting of such preparation; and
   g. raising the temperature of the environment in which the preparation from (f) is maintained to about 35° C. subliming the water from such preparation until the resulting amorphous cefazolin sodium has a moisture content of no more than 6 percent.

2. A method of preparing an ampoule of sterile, essentially amorphous cefazolin sodium for reconstitution for parenteral administration comprising the steps of:
   a. dissolving said cefazolin sodium in water in a concentration of from about 10 to about 25 percent (W/V);
   b. filtering the solution from (a) through a sterilizing filter into a previously sterilized container;
   c. filling a volume of the sterile solution from (b) into a previously sterilized ampoule such that the quantity of solute therein is the amount of cefazolin sodium desired in said ampoule;
   d. exposing the filled ampoule from (c) to an environment wherein the temperature is from about minus 50° C. to about minus 55° C.;
   e. cooling the filled ampoule from c) to a temperature wherein the frozen mass of the cefazolin sodium solution is reduced to minus 48° C. or below and stabilizing for about 30 minutes at such temperature;
   f. reducing the pressure of the environment in which the filled ampoule from (e) is maintained to a maximum of 100 microns Hg, and stabilizing such pressure for about 30 minutes;
   g. raising the temperature of the environment in which the filled ampoule from (f) is maintained to about 10° C. and holding such temperature until the temperature of the frozen mass of cefazolin sodium solution reaches about 5° C., avoiding the melting of such mass;
   h. raising the temperature of the environment in which the filled ampoule from (g) is maintained to about 35° C. subliming the water from such ampoule until the amorphous cefazolin sodium remaining therein has a moisture content of no more than 6 percent; and
   i. sterile stoppering and capping the resultant freeze-dried cefazolin sodium-containing ampoule.

* * * * *

UNITED STATES PATENT AND TRADEMARK OFFICE
CERTIFICATE OF CORRECTION

PATENT NO. : 4,002,748
DATED : January 11, 1977
INVENTOR(S) : Michael Bornstein et al.

It is certified that error appears in the above-identified patent and that said Letters Patent are hereby corrected as shown below:

Column 4, lines 5 and 6, "sodium a moisture" should read --sodium having a moisture--.

Column 5, line 49, "cefazolin solution" should read --cefazolin sodium solution--.

Signed and Sealed this

Seventh Day of June 1977

[SEAL]

Attest:

RUTH C. MASON
Attesting Officer

C. MARSHALL DANN
Commissioner of Patents and Trademarks